US008283490B2

(12) United States Patent
Ditzel et al.

(10) Patent No.: US 8,283,490 B2
(45) Date of Patent: *Oct. 9, 2012

(54) PROCESS FOR THE CARBONYLATION OF DIMETHYL ETHER

(75) Inventors: Evert Jan Ditzel, Goole (GB); David John Law, Beverley (GB)

(73) Assignee: BP Chemicals Limited, Middlesex (GB)

( * ) Notice: Subject to any disclaimer, the term of this patent is extended or adjusted under 35 U.S.C. 154(b) by 17 days.

This patent is subject to a terminal disclaimer.

(21) Appl. No.: 12/450,986

(22) PCT Filed: Apr. 23, 2008

(86) PCT No.: PCT/GB2008/001447
§ 371 (c)(1),
(2), (4) Date: Oct. 21, 2009

(87) PCT Pub. No.: WO2008/132450
PCT Pub. Date: Nov. 6, 2008

(65) Prior Publication Data
US 2010/0063315 A1 Mar. 11, 2010

(30) Foreign Application Priority Data
Apr. 26, 2007 (EP) .................................. 07251759

(51) Int. Cl.
*C07C 67/36* (2006.01)
(52) U.S. Cl. ...................................... 560/232; 560/129

(58) Field of Classification Search .................... None
See application file for complete search history.

(56) References Cited

U.S. PATENT DOCUMENTS

| 6,387,842 | B1 * | 5/2002 | Wegman et al. | 502/300 |
| 7,465,822 | B2 * | 12/2008 | Cheung et al. | 560/232 |
| 2006/0252959 | A1 * | 11/2006 | Cheung et al. | 560/232 |

FOREIGN PATENT DOCUMENTS
WO WO 2006/121778 11/2006

OTHER PUBLICATIONS

International Search Report for PCT/GB2008/001447, mailed Aug. 20, 2008.
Written Opinion of the International Searching Authority for PCT/GB2008/001447, mailed Aug. 20, 2008.
Cheung, P. et al., "Selective Carbonylation of Dimethyl Ether to Methyl Acetate Catalyzed by Acidic Zeolites", Angewandte Chemie Internation Edition, 45 (10), pp. 1617-1620, (2006).
Tartamella, T.L. et al, "Role of Acid Catalysis in Dimethyl Ether Conversion Processess", Proceedings—Annual International Pittsburgh Coal Conference, 13th (vol. 2), pp. 996-1001, (1996).

* cited by examiner

*Primary Examiner* — Sudhakar Katakam
(74) *Attorney, Agent, or Firm* — Nixon & Vanderhye

(57) ABSTRACT

Process for the production of methyl acetate by carbonylating a dimethyl ether feed with carbon monoxide in the presence of hydrogen under substantially anhydrous conditions, at a temperature in the range of greater than 250° C. to 350° C. and in the presence of a zeolite catalyst effective for said carbonylation. The concentration of dimethyl ether is at least 1 mol % based on the total feed.

13 Claims, 4 Drawing Sheets

Fig. 2 DME vs MeOH comparison

Fig. 3 DME vs MeOH comparison at 300 deg C

PROCESS FOR THE CARBONYLATION OF DIMETHYL ETHER

This application is the U.S. national phase of International Application No. PCT/GB2008/001447 filed 23 Apr. 2008, which designated the U.S. and claims priority to Europe Application No. 07251759.2 filed 26 Apr. 2007, the entire contents of each of which are hereby incorporated by reference.

This invention relates to a process for preparing methyl acetate by reacting dimethyl ether with carbon monoxide in the presence of a zeolite catalyst.

BACKGROUND OF THE INVENTION

Methyl acetate is used industrially in petrochemical processes, particularly as a feed for the production of acetic acid and/or acetic anhydride.

The commercial production of acetic acid is operated as a homogeneous liquid-phase process in which the carbonylation reaction is catalysed by a Group VIII noble metal such as rhodium or iridium and an alkyl iodide such as methyl iodide. The main drawbacks of this process are the use of iodide which can lead to corrosion problems and the difficulties associated with separation of the products and catalyst components from a single phase. Both of these drawbacks could be overcome if a heterogeneous gas phase process using an iodide free solid catalyst could be developed.

EP-A-0 596 632 describes a vapour phase process for the carbonylation of methanol to produce acetic acid in the presence of a modified mordenite catalyst at high temperatures and pressures.

WO 01/07393 describes a process for the catalytic conversion of a feedstock comprising carbon monoxide and hydrogen to produce at least one of an alcohol, ether and mixtures thereof and reacting carbon monoxide with the at least one of an alcohol, ether and mixtures thereof in the presence of a catalyst selected from solid super acids, heteropolyacids, clays, zeolites and molecular sieves, in the absence of a halide promoter, under conditions of temperature and pressure sufficient to produce at least one of an ester, acid, acid anhydride and mixtures thereof. However, the use of zeolites to catalyse the carbonylation reaction is not exemplified.

WO 2005/105720 describes a process for production of a carboxylic acid and/or an ester or anhydride thereof by carbonylating an aliphatic alcohol or reactive derivative thereof with carbon monoxide in the substantial absence of halogens in the presence of a modified mordenite catalyst at a temperature in the range 250-600° C. and a pressure in the range 10 to 200 bar. The use of dimethyl ether as a feedstock is not exemplified.

WO 2006/121778 describes a process for the production of a lower alkyl ester of a lower aliphatic carboxylic acid by carbonylating under substantially anhydrous conditions a lower alkyl ether with carbon monoxide in the presence of a mordenite or ferrierite catalyst. According to this patent application, the carbonylation process is run at temperatures at or below 250° C., and preferably from about 150 to about 180° C. to minimise by-product formation.

In Angewandte Chemie, Int. Ed. (2006), 45(10), 1617-1620, which describes the zeolite-catalysed carbonylation of dimethyl ether, it is demonstrated that at 165° C., increasing the concentration of dimethyl ether has no effect on the space time yield to methyl acetate product.

In view of the above-mentioned prior art, there remains the need for a heterogeneous gas phase process for the production of methyl acetate from dimethyl ether under substantially anhydrous conditions using a zeolite catalyst which is superior to the other processes using a carbonylatable reactant as a feed.

SUMMARY OF THE INVENTION

It has now been found that if the carbonylation process is carried out at a temperature in the range of greater than 250° C. to 350° C., in the presence of hydrogen and a dimethyl ether concentration of at least 1 mol % based on the total feed, higher catalytic activities are achieved.

Accordingly, the present invention provides a process for the production of methyl acetate which process comprises carbonylating, under substantially anhydrous conditions, a dimethyl ether feed with carbon monoxide in the presence of hydrogen, at a temperature in the range of greater than 250° C. to 350° C. and in the presence of a zeolite catalyst effective for said carbonylation, wherein the concentration of dimethyl ether is at least 1 mol % based on the total feed.

For a process to be commercially viable, the space time yield (STY) of the desired product must be of an acceptable value. In carbonylation processes, carbon monoxide is typically employed to carbonylate a reactant such as methanol or dimethyl ether. It has been found that in carbonylation processes employing methanol, carbon monoxide and a zeolite catalyst, that, increasing the concentration of methanol produces a decrease in STY. However, it has now been surprisingly found that in carbonylation processes employing dimethyl ether, carbon monoxide and a zeolite catalyst, increasing the concentration of dimethyl ether results in a corresponding increase in STY.

The dimethyl ether used as the feed in the process of the present invention may be substantially pure dimethyl ether. In commercial practice, dimethyl ether is produced by the catalytic conversion of synthesis gas (mixtures of hydrogen and carbon monoxide) over methanol synthesis and methanol dehydration catalysts. This catalytic conversion results in a product which is predominantly dimethyl ether but it may also contain some methanol. In the process of the present invention the dimethyl ether feed may comprise small amounts of methanol provided that the amount of methanol present in the feed is not so great as to inhibit the carbonylation of dimethyl ether to methyl acetate product. It has been found that 5 wt % or less, such as 1 wt % or less of methanol may be tolerated in the dimethyl ether feed.

The carbon monoxide may be substantially pure carbon monoxide, for example, carbon monoxide typically provided by suppliers of industrial gases, or it may contain impurities that do not interfere with the conversion of the dimethyl ether to methyl acetate, such as nitrogen, helium, argon, methane and/or carbon dioxide.

In the process of the present invention, hydrogen may be fed separately or together with the carbon monoxide. Mixtures of hydrogen and carbon monoxide are commercially produced by the steam reforming of hydrocarbons and by the partial oxidation of hydrocarbons. Such mixtures are commonly referred to as synthesis gas. Synthesis gas comprises mainly carbon monoxide and hydrogen but may also contain smaller quantities of carbon dioxide.

Suitably, the molar ratio of carbon monoxide:hydrogen may be in the range 1:3 to 15:1, such as 1:1 to 10:1, for example, 1:1 to 4:1.

In the process of the present invention, the concentration of dimethyl ether in the feed is at least 1 mol % based on the total gaseous feed. The feed may comprise solely dimethyl ether, hydrogen and carbon monoxide. However, as described above, commercial sources of carbon monoxide generally contain inert gases such as argon. Inert gases such as nitrogen and helium may also be present in the feed.

Where the process is to be operated as a continuous process, the feed will also include any process streams recycled to the reactor, such as unreacted carbon monoxide and/or unreacted dimethyl ether.

Suitably, dimethyl ether is present in the feed at a concentration in the range of 1 mol % to 20 mol %, for example, 1.5 mol % to 10 mol %, such as 1 to 5 mol % or 1.5 to 5 mol %, based on the total feed (including recycles).

The molar ratio of dimethyl ether to carbon monoxide is suitably in the range 1:1 to 1:99, such as 2:1 to 1:60.

The zeolite catalyst may be any zeolite which is effective to catalyse the carbonylation of dimethyl ether with carbon monoxide to produce methyl acetate.

Zeolites are available from commercial sources, generally in the Na, $NH_4$ form or H-form of the zeolite. The $NH_4$ form can be converted to the acid (H-form) by known techniques, such as calcination at high temperature. The Na form can be converted to the acid (H-form) by converting first to an $NH_4$ form by ion exchange with ammonium salts such as ammonium nitrate. Alternatively, zeolites may be synthesised using known techniques.

Zeolites comprise a system of channels which may be interconnected with other channel systems or cavities such as side-pockets or cages. The ring structures are generally 12-member rings, 10-member rings or 8 member rings. A zeolite may possess rings of different sizes. The zeolites for use in the present invention preferably contain at least one channel which is defined by an 8-member ring. Most preferably, the 8-member ring channel is interconnected with at least one channel defined by a ring with 10 and/or 12 members. The window size of the channel systems should be such that the reactant dimethyl ether and carbon monoxide molecules can diffuse freely in and out of the zeolite framework. Suitably, the window size of an 8-member ring channel may be at least 2.5×3.6 Angstroms. The *Atlas of Zeolite Framework Types* (C. Baerlocher, W. M. Meier, D. H. Olson, 5$^{th}$ ed. Elsevier, Amsterdam, 2001) in conjunction with the web-based version (http://www.iza-structure.org/databases/) is a compendium of topological and structural details about zeolite frameworks, including the types of ring structures present in a zeolite and the dimensions of the channels defined by each ring type. Examples of zeolites suitable for use in the present invention include zeolites of framework type MOR, for example mordenite, FER, such as ferrierite, OFF, for example, offretite and GME, for example gmelinite.

For the process of the present invention it is preferred that the zeolite has a silica to alumina ratio of at least 5 but preferably less than or equal to 100, such as in the range 7 to 40, for example 10 to 30. Where the aluminium atoms have been replaced by framework modifier elements such as gallium, it is preferred that the ratio of silica:$X_2O_3$ where X is a trivalent element, such as aluminium, gallium, iron and/or boron, is at least 5 and preferably less than or equal to 100, such as in the range 7 to 40, for example 10 to 30.

In one embodiment of the present invention the zeolite catalyst is a mordenite zeolite. The mordenite may be employed in the acid form (H-mordenite) or it may be optionally ion-exchanged or otherwise loaded with one or more metals such as copper, silver, nickel, iridium, rhodium, platinum, palladium or cobalt.

The metal loading on the mordenite zeolite may be expressed in terms of the fractional loading of the metal as gram atoms of metal per gram atom of aluminium in the mordenite. The metal loading can also be expressed as a mole percentage loading relative to aluminium in the mordenite through the relationship:

mol % Metal=(gram atoms Metal/gram atoms aluminium)×100

Thus, for example, a loading of 0.55 gram atoms of copper per aluminium in the mordenite equates to a 55 mol % loading of copper relative to aluminium in the mordenite.

Suitably, the metal loading may be in the range of 1 to 200 mol % relative to aluminium, such as 50 to 120 mol %, for example, 50 to 110 mol % or 55 to 120 mol %, such as 55 to 110 mol %.

The mordenite framework, may in addition to the silicon and aluminium atoms, contain additional trivalent elements, such as boron, gallium and/or iron.

Where the mordenite contains at least one or more trivalent framework, the metal loading in the mordenite can be expressed in terms of the fractional loading of the metal as gram atoms of metal per gram atom of total trivalent elements in the mordenite. The metal loading can also be expressed as a mole percentage loading relative to total trivalent elements in the mordenite through the relationship:

mol % Metal=(gram atoms Metal/gram atoms of total trivalent elements)×100

Because the carbonylation reaction is to be conducted substantially in the absence of water, it is preferred that the zeolite catalyst is dried prior to use. The zeolite may be dried, for example by heating to a temperature of 400 to 500° C.

It is preferred that the zeolite catalyst is activated immediately before use by heating the zeolite at elevated temperature for at least one hour under flowing nitrogen, carbon monoxide, hydrogen or mixtures thereof.

The process is carried out under substantially anhydrous conditions, i.e in the substantial absence of water. The carbonylation of dimethyl ether to methyl acetate does not generate water in-situ. Water has been found to inhibit the carbonylation of dimethyl ether to form methyl acetate. Thus, in the process of the present invention, water is kept as low as is feasible. To accomplish this, the dimethyl ether and carbon monoxide reactants (and catalyst) are preferably dried prior to introduction into the process. However, small amounts of water may be tolerated without adversely affecting the formation of methyl acetate. Suitably, water may be present in the dimethyl ether in amounts of 2.5 wt % or less, such as 0.5 wt % or less.

The process of the present invention is carried out at a temperature in the range of greater than 250 C to 350° C. Suitably, the temperature may be in the range 275 to 350° C. such as 275 to 325° C.

The process of the present invention may be carried out at a total reaction pressure of 1 to 100 barg, such as 10 to 100 barg, such as 30 to 100 barg.

The Gas Hourly Space Velocity (GHSV) is suitably in the range 500 to 40,000 $h^{-1}$, such as 2000 to 20,000 $h^{-1}$.

The process of the present invention is suitably carried out by passing dimethyl ether vapour and carbon monoxide gas through a fixed or fluidised bed of the zeolite catalyst maintained at the required temperature.

Preferably, the process of the present invention is carried out substantially in the absence of halides, such as iodide. By the term 'substantially' is meant that the halide, for example, iodide content of the reactant gases (dimethyl ether and carbon monoxide) and catalyst is less than 500 ppm, preferably less than 100 ppm.

The primary product of the process is methyl acetate but small amounts of acetic acid may also be produced. The methyl acetate produced by the process of the present invention can be removed in the form of a vapour and thereafter condensed to a liquid.

The methyl acetate may be recovered and sold as such or it may be forwarded to other chemical processes. Where the methyl acetate is recovered from the carbonylation reaction products, some or all of it may be hydrolysed to form acetic acid. Alternatively, the entire carbonylation reaction product may be passed to a hydrolysis stage and acetic acid separated thereafter. The hydrolysis may be carried out by known techniques such as reactive distillation in the presence of an acid catalyst.

The process may be operated as either a continuous or a batch process, preferably as a continuous process.

BRIEF DESCRIPTION OF THE DRAWINGS

The invention is further described with reference to the accompanying drawings, in which.

Figure 1:
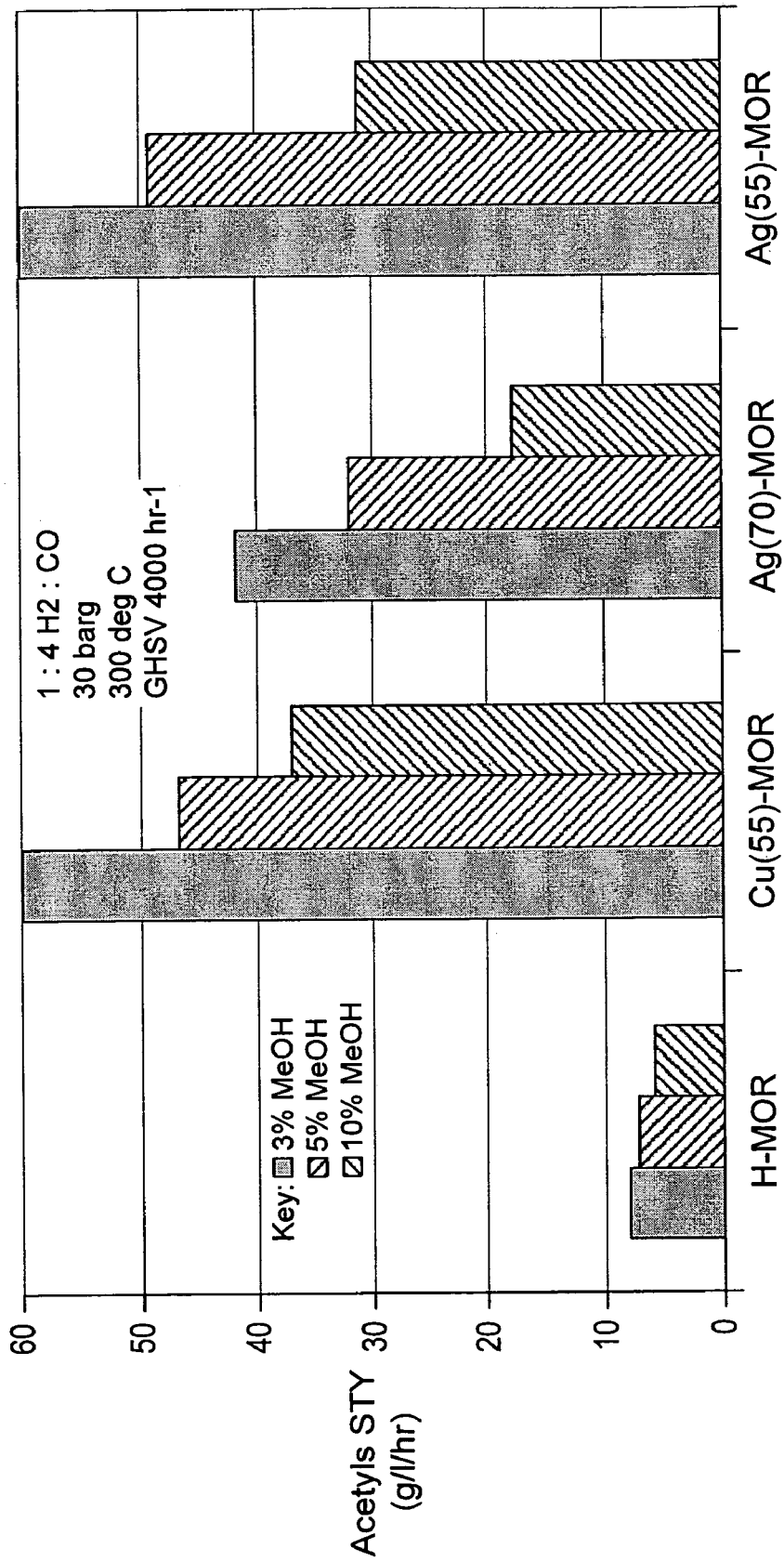
FIG. 1 is a plot showing that increasing the concentration of methanol results in a decrease in STY in regard to Experiment 1.

The invention is now illustrated with reference to the following Examples.

Catalyst Preparation
Catalyst A—H-Mordenite

H-Mordenite (H-MOR) with a silica to alumina ratio of 20 (ex Süd-chemie) was calcined in a muffle oven (oven-volume=18 L) under a static atmosphere of air. The temperature was increased from room temperature to 500° C. at a ramp rate of 5° C./min and then held at this temperature for 24 hours. The mordenite was then compacted at 12 tonnes in a 33 mm die set using a Specac Press, and then crushed and sieved to a particle size fraction of 212 to 335 microns.

Catalyst B—Cu-Mordenite—Cu(55)-MOR

H-Mordenite (40 g) with a silica to alumina ratio of 20 (ex Süd-chemie) was weighed into a 500 mL round bottomed flask together with 6.43 g of copper (II) nitrate hemipentahydrate (98% ACS) and a stirrer bar. Sufficient deionised water (ca. 100 mL) was then added to the flask until a thick slurry was obtained. The top of the flask was then loosely covered and the flask left to stir overnight. The copper loaded mordenite was then dried under reduced vacuum using a rotary evaporator before being dried in an oven at 100° C. for 12 hours. The zeolite was then calcined in a muffle oven (oven volume=18 L) under a static atmosphere of air. The temperature was increased from room temperature to 500° C. at a ramp rate of 5° C./min and then held at this temperature for 24 hours. The zeolite was then compacted at 12 tonnes in a 33 mm die set using a Specac Press, and then crushed and sieved to a particle size fraction of 212 to 335 microns. The mordenite had a Cu loading of 55 mole % of the amount of Al contained in the mordenite.

Catalyst C—Ag-Mordenite—Ag(55)-MOR

This zeolite was prepared in the same way as for Preparation B except that silver nitrate (99+% ACS) (7.16 g for 50 g mordenite) was used instead of copper (II) nitrate hemipentahydrate (98% ACS). The mordenite so prepared had a Ag loading of 55 mole % relative to aluminium.

Catalyst D—Ag-Mordenite—Ag(70)-MOR

This zeolite was prepared in the same way as for Preparation B except that silver nitrate (99+% ACS) (1.82 g for 10 g mordenite) was used instead of copper (II) nitrate hemipentahydrate (98% ACS). The mordenite so prepared had a Ag loading of 70 mole % relative to aluminium.

EXPERIMENT 1

Carbonylation of Methanol

Methanol was carbonylated with carbon monoxide in the presence of Catalysts A to D and hydrogen. The carbonylation reactions were carried out in a pressure flow reactor unit consisting of 60 identical parallel isothermal co-current tubular reactors of the type described in, for example, WO2006107187. The reactors were arranged in 4 blocks of 15 reactors, each block having an independent temperature control. Into each tube 25, 50 or 100 micro litres of catalyst (designed to give GHSVs corresponding to 8000, 4000 and 2000 $hr^{-1}$ respectively) was loaded onto a metal sinter having a pore size of 20 micrometers. The catalyst samples were heated at a ramp rate of 5° C./min. to 100° C. at atmospheric pressure under 98.8 mol % $N_2$ and 1.2 mol % He at a flow rate of 3.4 ml/min, and held at this temperature for 1 hour. The reactor was then pressurised to 30 barg with 98.8 mol % $N_2$ and 1.2 mol % He and the system held at this condition for 1 hour. The gas feed was then changed from the $N_2$ and He mixture to a mixture comprising 63.2 mole % carbon monoxide, 15.8 mole % hydrogen, 19.8 mole % nitrogen and 1.2 mol % helium at a gas flow rate of 3.4 ml/min, and the reactors were heated at a ramp rate 3° C./min. to a temperature of 300° C. The system was then held at this condition for 3 hours. After this the temperatures of blocks 1 to 4 were adjusted to 275, 300, 325 and 350° C. respectively, and the system was allowed to stabilise for 10 minutes. At this point catalyst activation was considered complete, and the gas feed was changed to a mixture comprising 63.2 mole % carbon monoxide, 15.8 mole % hydrogen, 14.8 mole % nitrogen, 1.2 mol % helium and 4.9 mole % methanol at a gas flow rate of 3.4 ml/min. The methanol was fed as a liquid to the inlet of each reactor where it evaporated to give the afore-mentioned gas feed composition. The experiment was then continued with the following gas mixtures.

| CO (mol %) | $H_2$ (mol %) | $N_2$ (mol %) | MeOH (mol %) | He (mol %) | Start time (hr) | Finish time (hr) |
|---|---|---|---|---|---|---|
| 63.2 | 15.8 | 14.8 | 4.9 | 1.2 | 0 | 37.3 |
| 63.2 | 15.8 | 9.90 | 9.9 | 1.2 | 37.3 | 65.5 |
| 63.2 | 15.8 | 14.8 | 4.9 | 1.2 | 65.5 | 92.1 |
| 63.2 | 15.8 | 16.8 | 3 | 1.2 | 92.1 | 119.5 |
| 63.2 | 15.8 | 14.8 | 4.9 | 1.2 | 119.5 | 136.1 |
| 63.2 | 15.8 | 9.9 | 9.9 | 1.2 | 136.1 | 152.5 |

The exit stream from the reactor was passed to two gas chromatographs. One of these was a Varian 4900 micro GC with three columns (Molecular sieve 5A, Porapak® Q, and CP-Wax-52) each quipped with a thermal conductivity detector. The other was an Interscience Trace GC with two columns (CP-Sil 5 and CP-Wax 52) each equipped with a flame ionisation detector.

Averaged STY results for 92.1 to 152.5 hours are shown in FIG. 1. $STY_{acetyls}$ is defined as the STY for the production of AcOH plus the STY for the production of MeOAc multiplied by $MW_{AcOH}/MW_{MeOAc}$.

FIG. 1 clearly demonstrates that increasing the concentration of methanol results in a decrease in STY.

EXAMPLE 1

Carbonylation of Dimethyl Ether

Dimethyl ether was carbonylated with carbon monoxide in the presence of Catalysts A to D in the presence of hydrogen. The carbonylation reactions were carried out in a pressure flow reactor unit consisting of 60 identical parallel isothermal co-current tubular reactors of the type described in, for example, WO2006107187. The reactors were arranged in 4 blocks of 15 reactors, each block having an independent temperature control. Into each reactor tube 25, 50 or 100 micro litres of catalyst (designed to give GHSVs corresponding to 8000, 4000 and 2000 hr$^{-1}$ respectively) was loaded onto a metal sinter having a pore size of 20 micrometers. The catalyst samples were heated at a ramp rate of 5° C./min. to 100° C. at atmospheric pressure under 98.6 mol % $N_2$ and 1.4 mol % He at a flow rate of 3.4 ml/min, and held at this temperature for 1 hour. The reactor was then pressurised to 30 barg with 98.6 mol % $N_2$ and 1.4 mol % He and the system held at this condition for 1 hour. The gas feed was then changed from the $N_2$ and helium mix to a mixture comprising 63.1 mol % carbon monoxide, 15.8 mol % hydrogen, 19.7 mol % nitrogen and 1.4 mol % helium at a gas flow rate of 3.4 ml/min, and the reactors were heated at a ramp rate 3° C./min. to a temperature of 300° C. The system was then held at this condition for 3 hours. Subsequently, the temperatures of blocks 1 to 4 were adjusted to 275, 300, 325 and 350° C. respectively, and the system was allowed to stabilise for 10 minutes. At this point catalyst activation was considered complete, and the gas feed was changed to a mixture comprising 63.1 mol % carbon monoxide, 15.8 mol % hydrogen, 14.8 mol % nitrogen, 1.4 mol % helium and 4.9 mol % dimethyl ether at a gas flow rate of 3.4 ml/min. The reaction was allowed to continue for ca. 93 hours. The exit stream from the reactor was passed to two gas chromatographs. One of these was a Varian 4900 micro GC with three columns (Molecular sieve 5A, Porapak® Q, and CP-Wax-52) each quipped with a thermal conductivity detector. The other was an Interscience Trace GC with two columns (CP-Sil 5 and CP-Wax 52) each equipped with a flame ionisation detector. STY and selectivity data was averaged over a 27 hour period from 65 to 93 hours.

EXAMPLE 2

Carbonylation of Dimethyl Ether

Example 1 was repeated using 50, 100 or 200 micro litres of Catalysts A-D and a combined gas flow of 6.8 ml/min. For the carbonylation reactions the temperatures of blocks 1 to 4 were 220; 250, 300 and 350° C. respectively. After 154.4 hours the following experiment to test the effect of changing the DME concentration was conducted. At this stage the gas feed was comprised of 63.1 mol % carbon monoxide, 15.8 mol % hydrogen. 14.8 mol % nitrogen, 1.4 mol % helium and 4.9 mol % dimethyl ether. The reactor was allowed to continue for 21.5 hours at which stage the gas feed was changed to 63.1 mol % carbon monoxide, 15.8 mol % hydrogen, 17.3 mol % nitrogen, 1.4 mol % helium and 2.5 mol % dimethyl ether. The system was allowed to run under these conditions for 28 hours at which stage the gas feed was changed to a mixture comprising 63.1 mol % carbon monoxide, 15.8 mol % hydrogen, 18.2 mol % nitrogen, 1.4 mol % helium and 1.5 mol % dimethyl ether. The system was then run under these conditions for 28.5 hours. STY data was averaged over the relevant time period to generate the STY results at each of 5 mol %, 2.5 mol % and 1.5 mol % dimethyl ether. The STY results are given in Tables 1 to 3 below. $STY_{acetyls}$ is defined as the STY for the production of AcOH plus the STY for the production of MeOAc multiplied by $MW_{AcOH}/MW_{MeOAc}$.

TABLE 1

| 250 Deg C. | $STY_{acetyls}$ (g/lcat/hr) 1.5% DME | $STY_{acetyls}$ (g/lcat/hr) 2.5% DME | $STY_{acetyls}$ (g/lcat/hr) 5% DME |
|---|---|---|---|
| H-MOR - 50 µl | 2.9 | 2.8 | 3.5 |
| H-MOR - 100 µl | 2.9 | 2.7 | 3.9 |
| H-MOR - 200 µl | 2.7 | 2.8 | 3.5 |
| Cu(55)-MOR - 50 µl | 7.1 | 8.2 | 11.7 |
| Cu(55)-MOR - 100 µl | 9.9 | 10.2 | 14.4 |
| Cu(55)-MOR - 200 µl | 10.4 | 11.3 | 17.9 |
| Ag(55)-MOR - 50 µl | 11.9 | 12.9 | 16.6 |
| Ag(55)-MOR - 100 µl | 11.3 | 12.2 | 15.7 |
| Ag(55)-MOR - 200 µl | 12.0 | 12.9 | 17.3 |

TABLE 2

| 300 Deg C. | $STY_{acetyls}$ (g/lcat/hr) 1.5% DME | $STY_{acetyls}$ (g/lcat/hr) 2.5% DME | $STY_{acetyls}$ (g/lcat/hr) 5% DME |
|---|---|---|---|
| H-MOR - 50 µl | 10.8 | 13.3 | 18.0 |
| H-MOR - 100 µl | 14.9 | 15.3 | 20.0 |
| H-MOR - 200 µl | 15.2 | 17.6 | 19.9 |
| Cu(55)-MOR - 50 µl | 30.0 | 31.5 | 47.5 |
| Cu(55)-MOR - 100 µl | 42.2 | 48.9 | 67.0 |
| Cu(55)-MOR - 200 µl | 45.1 | 56.0 | 81.2 |
| Ag(55)-MOR - 50 µl | 43.7 | 43.1 | 56.7 |
| Ag(55)-MOR - 100 µl | 33.2 | 39.7 | 57.3 |
| Ag(55)-MOR - 200 µl | 29.0 | 39.6 | 54.4 |

TABLE 3

| 350 Deg C. | $STY_{acetyls}$ (g/lcat/hr) 1.5% DME | $STY_{acetyls}$ (g/lcat/hr) 2.5% DME | $STY_{acetyls}$ (g/lcat/hr) 5% DME |
|---|---|---|---|
| H-MOR - 50 µl | 12.8 | 15.1 | 19.3 |
| H-MOR - 100 µl | 14.8 | 17.6 | 22.5 |
| H-MOR - 200 µl | 12.3 | 15.0 | 20.2 |
| Cu(55)-MOR - 50 µl | 59.6 | 72.5 | 90.1 |
| Cu(55)-MOR - 100 µl | 58.5 | 71.0 | 101.3 |
| Cu(55)-MOR - 200 µl | — | — | — |
| Ag(55)-MOR - 50 µl | 32.4 | 38.3 | 52.0 |
| Ag(55)-MOR - 100 µl | 38.3 | 50.6 | 65.0 |
| Ag(55)-MOR - 200 µl | 34.7 | 46.3 | 62.7 |

Tables 1-3 demonstrate that increasing the concentration of dimethyl ether results in an improves STY.

EXAMPLE 3

Figure 2:
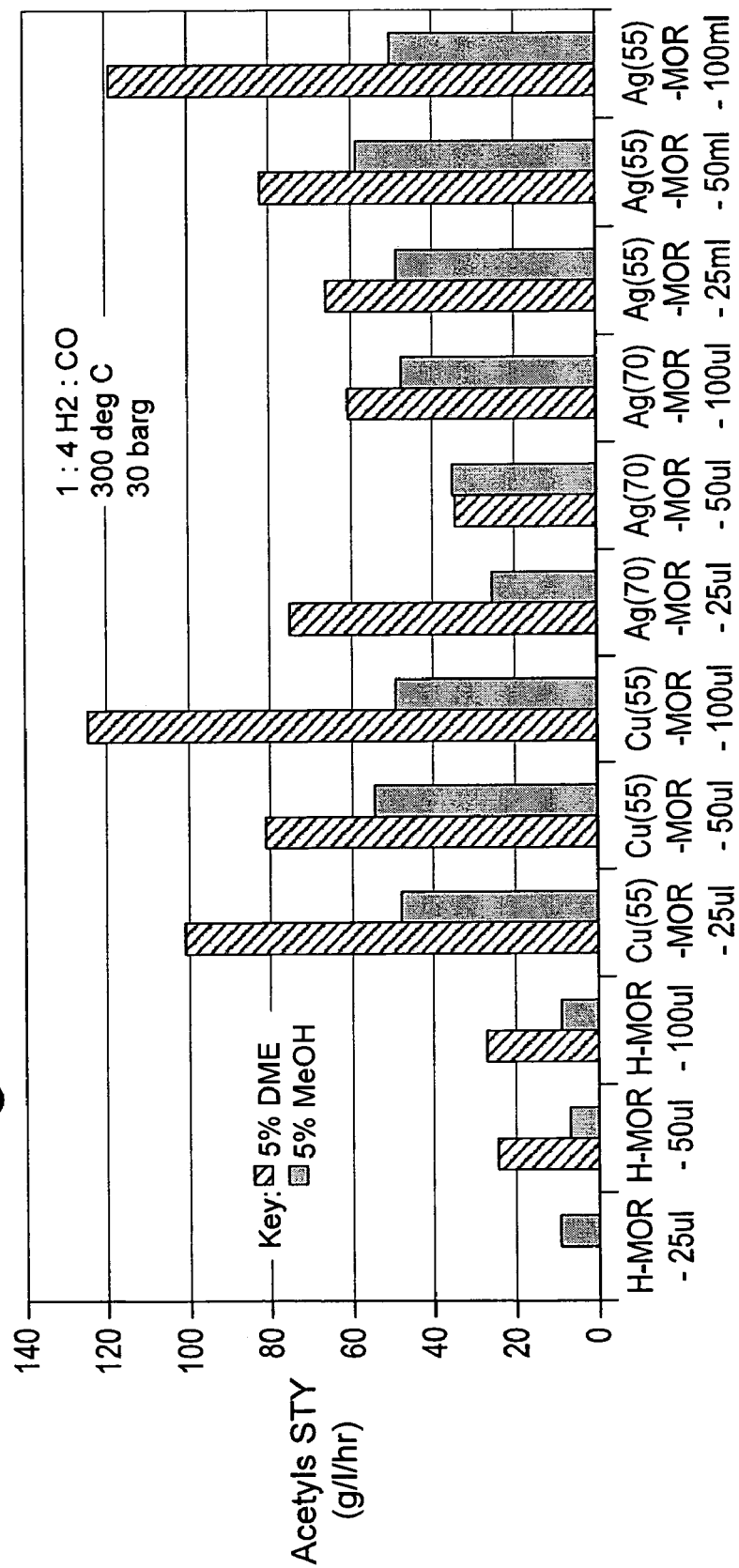
FIG. 2 is a plot showing the STY and selectivity data for reactions for the time period 65-92 hours in regard to Example 3.
Figure 3:
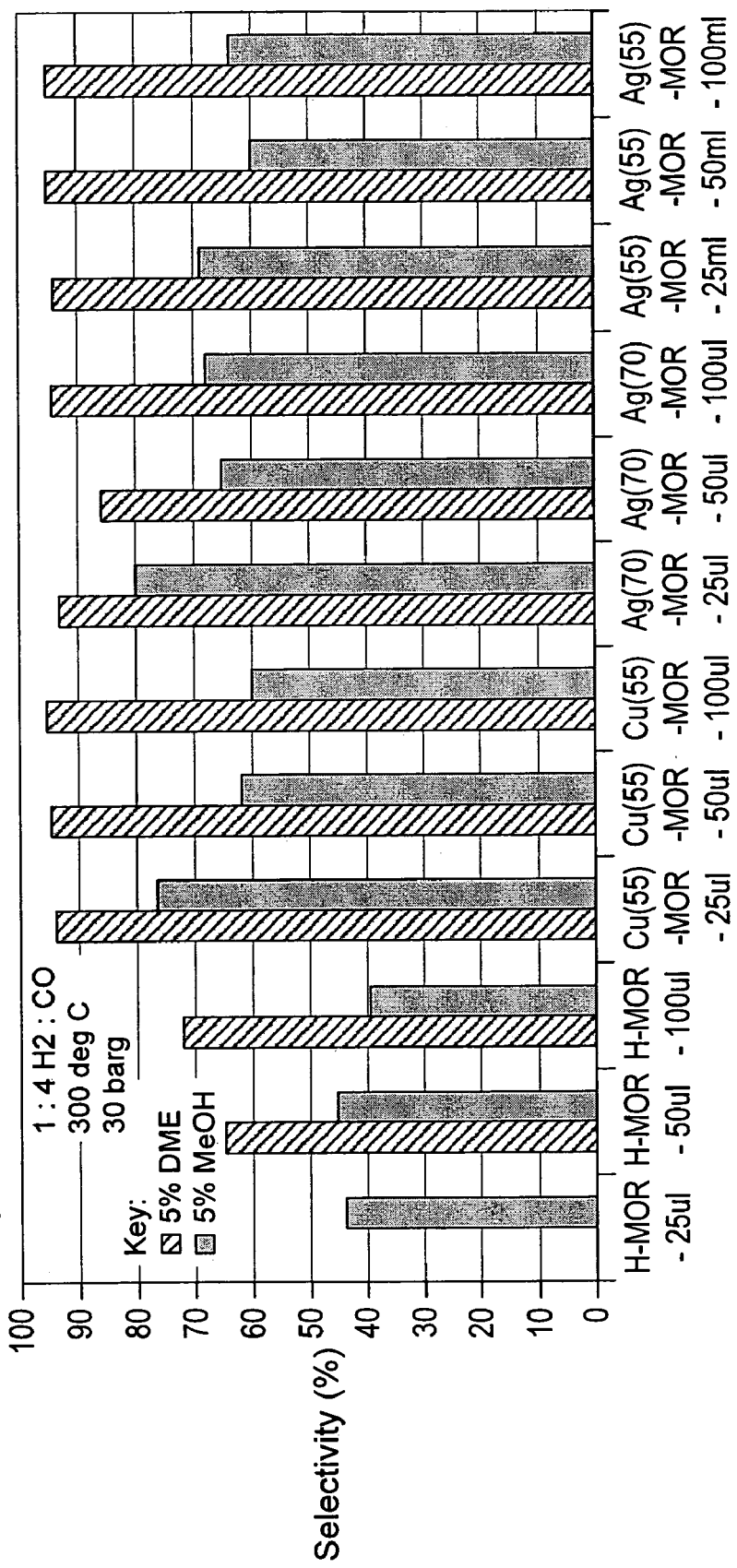
FIG. 3 is a plot showing the selectivity results for the reactions referred to in FIG. 2 and Example 3.

In each of Experiment 1 and Example 1, carbonylation reactions were carried out at 300° C., using 5 mol % methanol and 5 mol % dimethyl ether respectively. The STY and selectivity data for these reactions for the time period 65-92 hours are shown in FIG. 2 and the selectivity results are shown in FIG. 3.

$STY_{acetyls}$ is defined as the STY for the production of AcOH plus the STY for the production of MeOAc multiplied by $MW_{AcOH}/MW_{MeOAc}$.

For methanol carbonylation:

Selectivity=([MeOAc]out+[AcOH]out)/([MeOH]in−
[MeOH]out−(2*[Me2O]out)−[MeOAc]out)*100

For dimethyl ether carbonylation:

Selectivity=([MeOAc]out+[AcOH]out)/([DME]in−[DME]out−0.5*[MeOH]out)−0.5*[MeOAc]out)* 100

From an inspection of FIGS. 2 and 3 it can be seen that the carbonylation of 5 mol % dimethyl ether produces superior STY and selectivity results compared to a carbonylation process employing an equivalent concentration of methanol.

EXAMPLE 4

Figure 4:
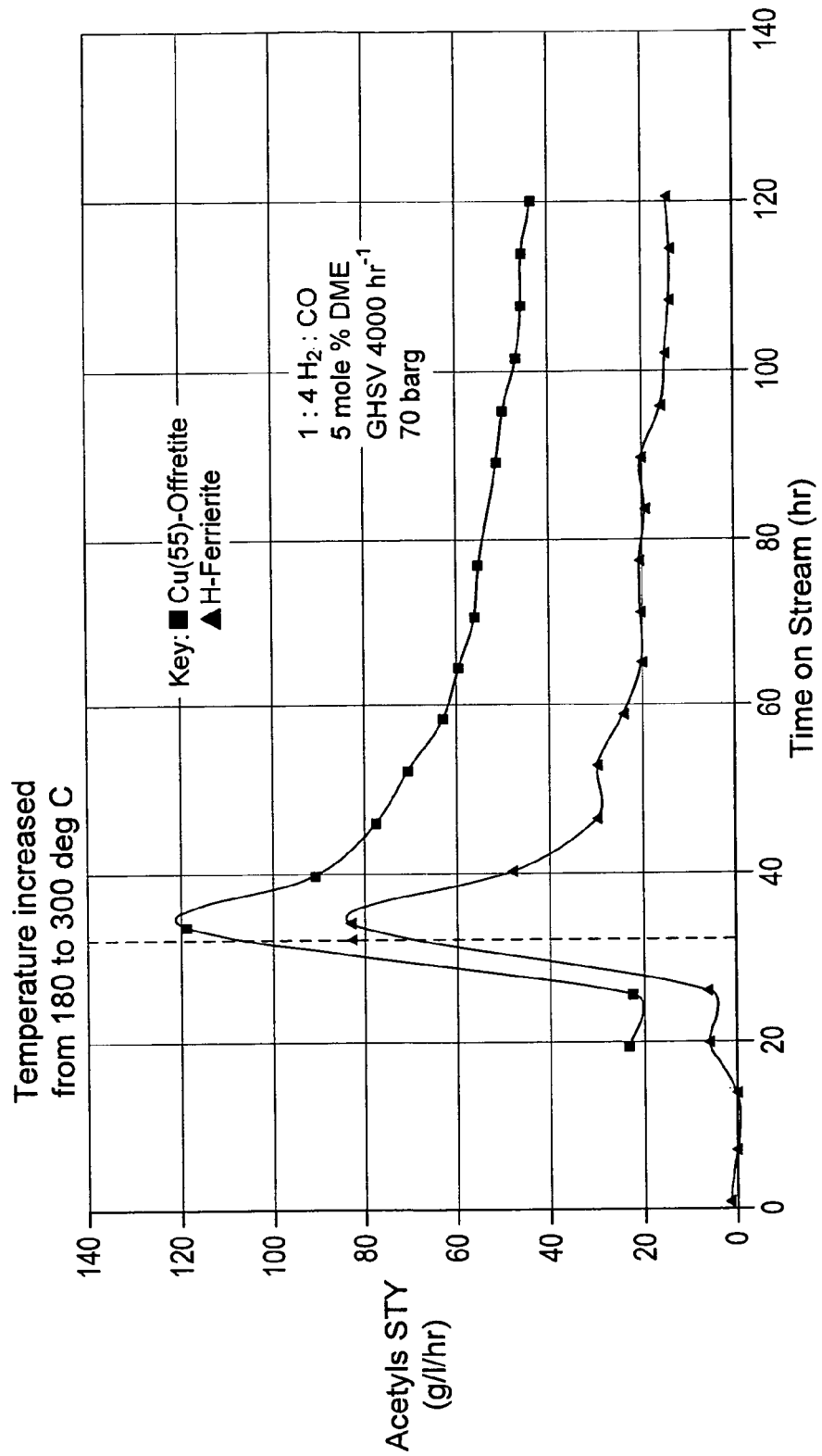
FIG. 4 are plots showing the STY results for the reactions discussed in Example 4.

Catalyst Preparation
Catalyst E—H-Ferrierite
$NH_4$-Ferrierite with a silica to alumina ratio of 55 (ex Zeolyst) was calcined in a muffle oven under a static atmosphere of air. The temperature was increased from room temperature to 110° C. at a ramp rate of 5° C./min. and held at this temperature for 2 hours. The temperature was then increased to 450° C. at a ramp rate of 5° C./min and held at this temperature for 12 hours. The H-ferrierite was then compacted at 12 tonnes in a 33 mm die set using a Specac Press, and then crushed and sieved to a particle size fraction of 212 to 335 microns.
Catalyst F—Cu-Offretite—Cu(55)-Offretite
To 0.3 grams of $NH_4$-Offretite with a silica to alumina ratio of 10 (ex Sintef) was added 430 micro litres of a solution containing 0.3 grams of copper (II) nitrate hemipentahydrate (98% ACS) per ml of water. Additional water (to make the total amount of solution added up to ca. 700 micro litres) was added at the same time and the resultant slurry agitated on a roller bench for at least 1 hour to ensure thorough mixing. The zeolite was then dried at 50° C. for at least 16 hours, then at 110° C. for 4 hours before being calcined in a muffle furnace under a static atmosphere of air. The temperature for calcination was increased from room temperature to 500° C. at a rate of 2° C./min. and then held at this temperature for 2 hours. The Cu loaded offretite was then compacted at 12 tonnes in a 33 mm die set using a Specac Press, and then crushed and sieved to a particle size fraction of 212 to 335 microns. The Cu-offretite had a Cu loading of ca. 55 mole % relative to Al contained in the offretite.
Carbonylation of Dimethyl Ether
Example 1 was repeated using 50 micro litres of catalysts E and F in the reactors (designed to give a GHSV of 4000 $hr^{-1}$), at a pressure of 70 barg. After holding the temperature of the reactors at 300° C. for 3 hours the temperature was adjusted to 180° C. and the system allowed to stabilise for 10 minutes before the gas feed was changed to a mixture comprising 63.1 mol % carbon monoxide, 15.8 mol % hydrogen, 14.8 mol % nitrogen, 1.4 mol % helium and 4.9 mol % dimethyl ether at a gas flow rate of 3.4 ml/min. The reaction was allowed to run under these conditions for 32.2 hours before the temperature was increased to 300° C. Reaction was then allowed to continue for a further 88 hours. The STY results are depicted in FIG. 4.

The invention claimed is:

1. A process for the production of methyl acetate which process comprises carbonylating a dimethyl ether feed with carbon monoxide in the presence of hydrogen under substantially anhydrous conditions, at a temperature in the range of 275° C. to 350° C. and in the presence of a zeolite catalyst effective for said carbonylation, wherein the concentration of dimethyl ether is at least 1 mol % based on the total feed.

2. A process according to claim 1 wherein the concentration of dimethyl ether is 1.5 to 10 mol % based on the total feed.

3. A process according to claim 2 wherein the concentration of dimethyl ether is 1.5 to 5 mol % based on the total feed.

4. A process according claim 1 wherein the zeolite contains at least one channel which is defined by an 8-member ring.

5. A process according to claim 4 wherein the 8-member ring channel is interconnected with at least one channel defined by a ring with 10 and/or 12 members.

6. A process according to claim 1 wherein the zeolite is selected from the group consisting of mordenite, ferrierite, offretite and gmelinite.

7. A process according to claim 6 wherein the mordenite is selected from Hmordenite or a mordenite ion-exchanged or otherwise loaded with at least one metal selected from the group consisting of copper, nickel, iridium, silver, rhodium, platinum, palladium and cobalt.

8. A process according to claim 7 wherein the mordenite is loaded with a metal selected from the group consisting of copper, silver and mixtures thereof.

9. A process according to claim 7 wherein the mordenite is loaded with the metal in the range 55 to 120 mol % relative to aluminium.

10. A process according to claim 1 wherein the process is carried out at a pressure in the range 10 to 100 barg.

11. A process according claim 1 wherein the molar ratio of carbon monoxide:hydrogen is in the range 1:3 to 15:1.

12. A process according to claim 1 wherein at least some of the methyl acetate product is hydrolysed to acetic acid.

13. A process according to claim 1 wherein the process is carried out in the presence of a mordenite zeolite and the concentration of dimethyl ether is in the range 1.5 to 5 mol % based on the total feed.

* * * * *